(12) United States Patent
McNeese et al.

(10) Patent No.: US 12,369,858 B2
(45) Date of Patent: Jul. 29, 2025

(54) DEVICE FOR MONITORING AND MEASURING CONCUSSIONS AND HEAD IMPACT

(71) Applicants: Marc McNeese, St. Augustine, FL (US); Shandra McNeese, St. Augustine, FL (US)

(72) Inventors: Marc McNeese, St. Augustine, FL (US); Shandra McNeese, St. Augustine, FL (US)

( * ) Notice: Subject to any disclaimer, the term of this patent is extended or adjusted under 35 U.S.C. 154(b) by 0 days.

(21) Appl. No.: 18/636,171

(22) Filed: Apr. 15, 2024

(65) Prior Publication Data

US 2024/0341683 A1    Oct. 17, 2024

Related U.S. Application Data

(60) Provisional application No. 63/459,281, filed on Apr. 14, 2023.

(51) Int. Cl.
*A61B 5/00* (2006.01)
*A61B 5/11* (2006.01)
*A63B 71/08* (2006.01)

(52) U.S. Cl.
CPC .............. *A61B 5/682* (2013.01); *A61B 5/002* (2013.01); *A61B 5/1114* (2013.01); *A63B 71/081* (2013.01)

(58) Field of Classification Search
CPC ....... A61B 5/682; A61B 5/002; A61B 5/1114; A63B 71/081
See application file for complete search history.

(56) References Cited

U.S. PATENT DOCUMENTS

| | | | | |
|---|---|---|---|---|
| 5,293,880 | A * | 3/1994 | Levitt | A63B 71/085 128/862 |
| 2012/0172679 | A1* | 7/2012 | Logan | A61B 5/6803 600/301 |
| 2014/0323921 | A1* | 10/2014 | Huang | A61B 5/103 600/587 |
| 2017/0071526 | A1* | 3/2017 | Lyren | A63B 71/085 |
| 2022/0280108 | A1* | 9/2022 | Gonzales | A61B 5/7282 |
| 2022/0331065 | A1* | 10/2022 | Shah | A61B 5/02055 |
| 2023/0000665 | A1* | 1/2023 | Ghuge | A61N 1/0548 |

* cited by examiner

*Primary Examiner* — Alex M Valvis
*Assistant Examiner* — Anna Roberts
(74) *Attorney, Agent, or Firm* — Intellectual Property Consulting, LLC; Mark N. Melasky; Jared K. Rovira

(57) ABSTRACT

A device for measuring parameters associated with concussions due to impacts to the head of a person using a mouthpiece with a sensor that is configured to contact one or more bones of a person's face, such as the maxilla bone. The device may include a number of inflatable air pockets to aid in retaining the position of the sensor. The device may further include a sensor that contacts the exterior of a person's cranium and a communication module for transmitting the sensor readings. The device may be hinged in such a way that users may still easily talk and breathe.

20 Claims, 6 Drawing Sheets

DEVICE FOR MONITORING AND MEASURING CONCUSSIONS AND HEAD IMPACT

PRIORITY

This application claims benefit of U.S. Provisional Patent Application Ser. No. 63/459,281 filed Apr. 14, 2023, the entirety of which is incorporated by reference as if fully disclosed herein.

FIELD OF THE INVENTION

The present invention relates generally to the field of monitoring and measuring impacts on the head and concussions of participants in sports.

GENERAL BACKGROUND

Concussions and Chronic Traumatic Encephalopathy (CTE) are significant concerns in contact sports due to their potential long-term effects on athletes' health. Contact sports such as American football, soccer, ice hockey, rugby, boxing, and mixed martial arts involve a high risk of concussions and CTE due to the head injuries inherent to the physical nature of the games. Efforts to prevent concussions and reduce the risk of CTE include rule changes in sports leagues, improved equipment design, education for coaches, athletes, and parents, and better concussion management protocols. While it is recognized that immediate removal from play after a concussion and proper medical evaluation are critical in preventing further injury and promoting recovery, it can be difficult to know whether a player has experienced a concussion due to the subjective and case-by-case nature of the type and severity of symptoms present in concussions. Effectively determining when a player needs to be removed from game may be further hindered by a player's own insistence that they are not injured. Therefore, there exists a need for a means of consistently and objectively determining, in real-time, when a player has experienced a concussion.

SUMMARY OF THE INVENTION

In accordance with some embodiments, the present invention is a device for measuring parameters associated with concussions due to impacts to the head of a person comprising at least a mouthpiece with a sensor in contact with one or more bones of a person's face. In some embodiments the device may further include a sensor that contacts the exterior of a person's cranium.

BRIEF DESCRIPTION OF THE DRAWINGS

The foregoing and other objects, features, and advantages of the invention are apparent from the following detailed description taken in conjunction with the accompanying drawings in which like parts are given like reference numerals and, wherein:

FIG. 7 depicts a view of computer module and external sensor in accordance with embodiments of the invention.

Figure 1:
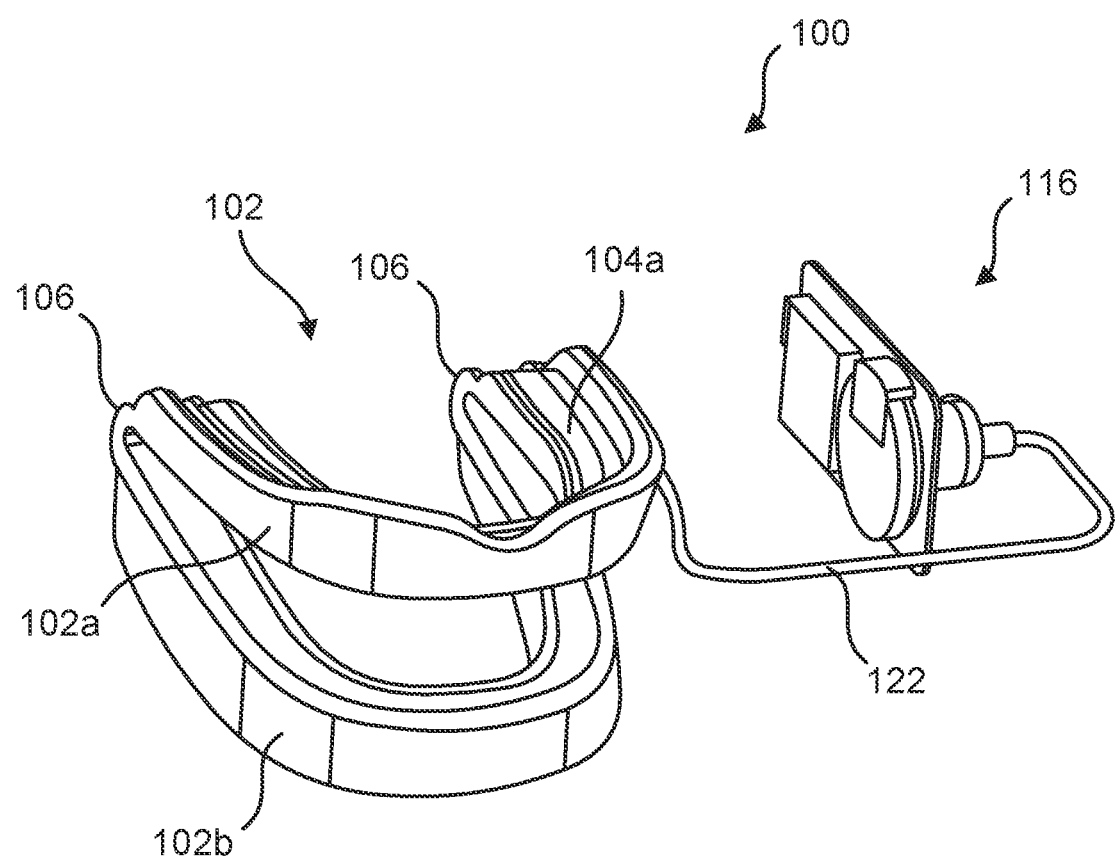
FIG. 1 depicts an angled view of the device in accordance with embodiments of the invention.

The images in the drawings are simplified for illustrative purposes and are not depicted to scale. Within the descriptions of the figures, similar elements are provided similar names and reference numerals as those of the previous figure(s). The specific numerals assigned to the elements are provided solely to aid in the description and are not meant to imply any limitations (structural or functional) on the invention.

The appended drawings illustrate exemplary configurations of the invention and, as such, should not be considered as limiting the scope of the invention that may admit to other equally effective configurations. It is contemplated that features of one configuration may be beneficially incorporated in other configurations without further recitation.

DETAILED DESCRIPTION

The embodiments of the disclosure will be best understood by reference to the Figures, wherein like parts are designated by like numerals throughout. It will be readily understood that the components, as generally described and illustrated in the Figures herein, could be arranged and designed in a wide variety of different configurations or be entirely separate. Thus, the following more detailed description of the embodiments of the device of the disclosure, as represented in the Figures is not intended to limit the scope of the disclosure, as claimed, but is merely representative of possible embodiments of the disclosure.

The following description sets forth numerous embodiments and parameters. It should be recognized, however, that such description is not intended as a limitation on the scope of the present invention but is instead provided as a description of exemplary embodiments. Various modifications to the examples described will be readily apparent to those of ordinary skill in the art, and the general principles defined may be applied to other examples and applications without departing from the spirit and scope of the invention. Thus, the present invention is not intended to be limited to the examples described herein but is to be accorded a scope consistent with the claims.

Concussions are significant concerns in contact sports due to their potential long-term effects on athletes' health. Concussions are a type of traumatic brain injury caused by a sudden blow or jolt to the head or body, which causes the brain to move rapidly within the cranium. Repeated concussions, especially if they occur before the brain has fully healed from previous injuries, can increase the risk of long-term complications, including cognitive problems, memory issues, and increased susceptibility to further injury. Thus, it is essential to take concussions seriously and take steps to prevent them whenever possible, such as wearing appropriate protective gear during sports and following safety guidelines in other activities. Determining when a concussion has taken place can be difficult, however, because not patients suffer the same symptoms or to the same degree. In fact, it is possible for someone suffering from a concussion to exhibit no symptoms at all. In the area of sports, the unreliability of concussion diagnosis is exacerbated by a hectic environment that lends itself to rushed evaluations by players and staff alike, as well as a player's willingness to downplay symptoms and 'tough out' their injuries. Therefore, there is a serious need for more objective indicators that can help determine when a player has received a concussion and needs to be removed from play to prevent further injury.

One way to provide objectivity in concussion diagnosis is by measuring the parameters associated with an impact to the head and the surrounding areas. Many measurements can be used to help quantify the severity of one or more head impacts, and thus the resultant impact(s) on the brain. Measurements such as force, acceleration, impact, pressure, velocity, impulse, direction and/or momentum can be used to help evaluate a concussion. Measuring the initial impact on the head provides critical information in understanding the potential existence and likely severity of a concussion.

While a quantification of the initial impact is a useful tool, it does not provide a comprehensive analysis of the concussion event. Often during such a concussion event, and following the initial external impact on the head, the brain will then impact against the inside of the cranium, this impact is referred to as a coup. After the coup, a subsequent impact against the opposite side of the cranium may occur, called a counter coup. The coup and counter coup provide detectable, measurable vibrations on the bones of the cranium. Measuring the parameters surrounding the coup and counter coup events during a concussion event can provide critical information when diagnosing a concussion. The measurement of multiple actions in the wider concussion events provides a more complete and accurate report of the concussion. This accuracy can be further increased by measuring parameters at multiple points and multiple bones in the cranium. This information can be used to help determine the likelihood of whether or not a player has had a concussion, the severity of that concussion and whether a player should be pulled from a game or event. Further, this information can be collected, studied and used to develop criteria and protocols surrounding concussion in sports.

It is further necessary that the measurements and outputs of the concussion devices are able to be remotely monitored in real-time by staff and trainers, so that alerts and outputs can be provided to staff, trainers and coaches instantly and proper health decisions can be made as quickly as possible.

One problem with many current devices for the detection and measurement of concussions is that they only account for the initial impact of a concussion event and do not measure the coup and counter coup. Further, some systems contain poor sensor locations or direct sensors to nonoptimal points on the cranium for measurement. Some devices only measure the impact that the helmet receives and do not directly measure the impact on the cranium. The impact imparted to the helmet may provide an approximation of the impact sustained by a cranium, however, there are many variables that may prevent consistent prediction of the cranium and brain impact based on the impact received by the helmet. This problem can be improved by placing a sensor in the interior of the helmet that directly contacts the exterior of the head. However, there are problems with systems that rely solely on this method. Poor contact between sensor and the head caused by poor helmet fit, hair or sweat may compromise the accuracy of the result. The present device cures many of these problems The device comprises a mouthpiece with at least one sensor that is in close proximity or direct contact with one or more bones around the mouth. In some embodiments, the one or more sensors directly contacts or is held in close proximity to the maxilla bone of a person's face. In some embodiments, the one or more sensors directly contacts or is held in close proximity to the mandible bone of a person's face. In some embodiments, the one or more sensors directly contacts or is held in close proximity to the temple of a user's cranium.

When a concussion event occurs, the force of the one or more external impacts and the coup and counter coup of the brain create measurable signatures in the bones of the cranium including the maxilla of the face and the mandible of the face. The one or more sensors of the device may be any suitable form of sensor suitable for measuring these signatures. The sensors may measure force, linear acceleration, radial acceleration, acceleration translation, impact, pressure, velocity, impulse, bone induction/conduction, vibration or any other parameters associated with concussions, CTE, and/or head injuries. In some embodiments, the sensor is a high, medium or low impact sensor. In some embodiments, the sensor is in the shape of a wire, such as a pressure wire. In some embodiments, the device may compromise more than one form of sensor.

Figure 2:
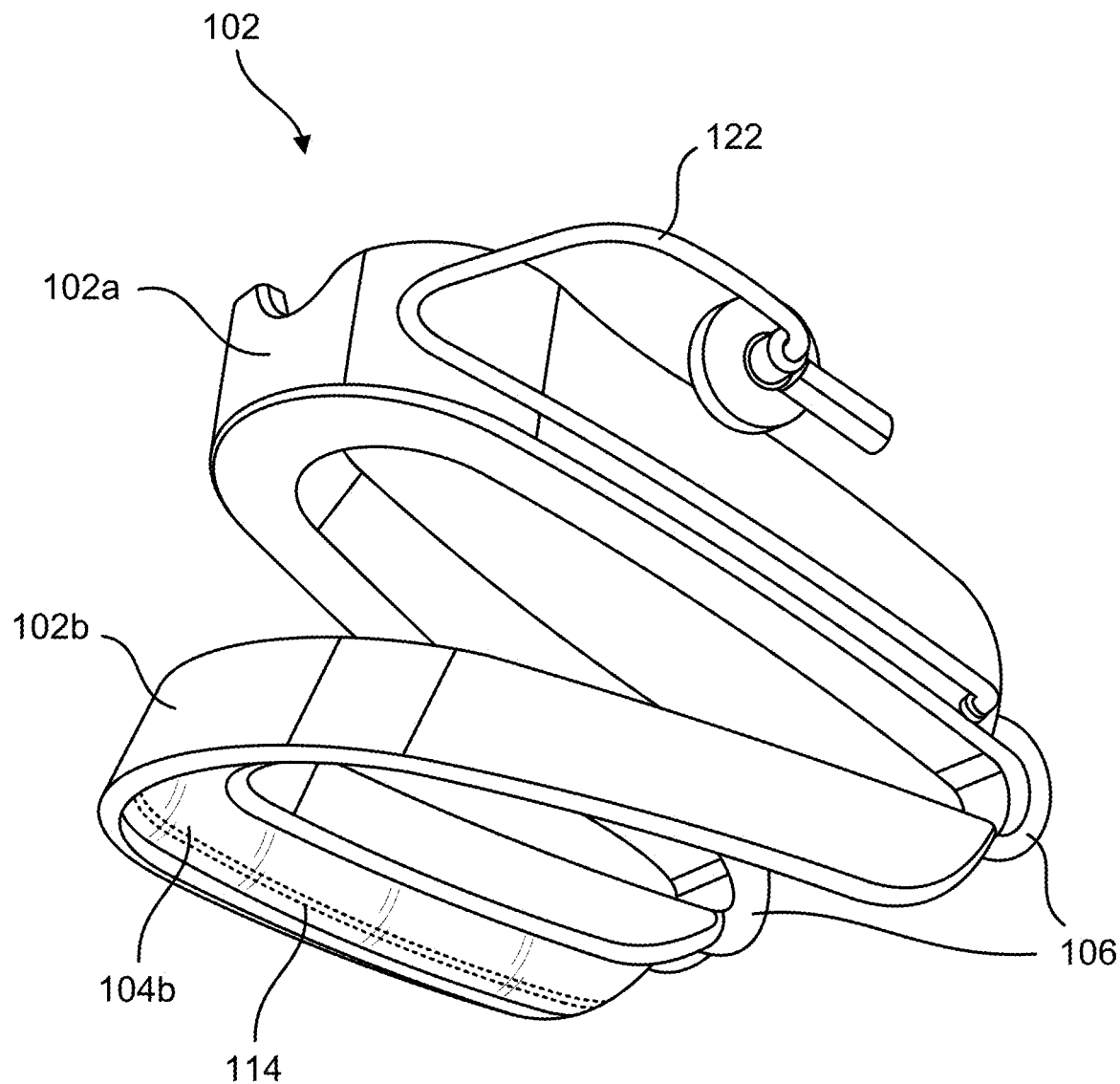
FIG. 2 depicts an angled side view of the device in accordance with embodiments of the invention.
Figure 3:
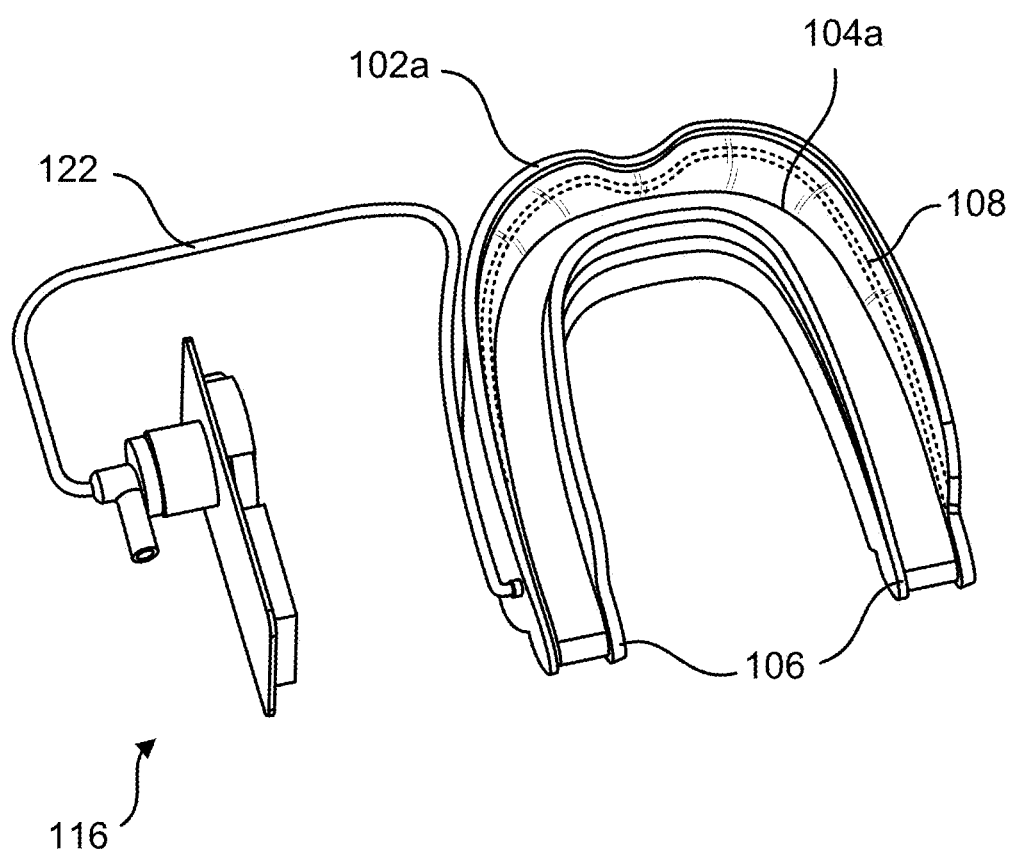
FIG. 3 depicts an angled top view of the device in accordance with embodiments of the invention.
Figure 4:
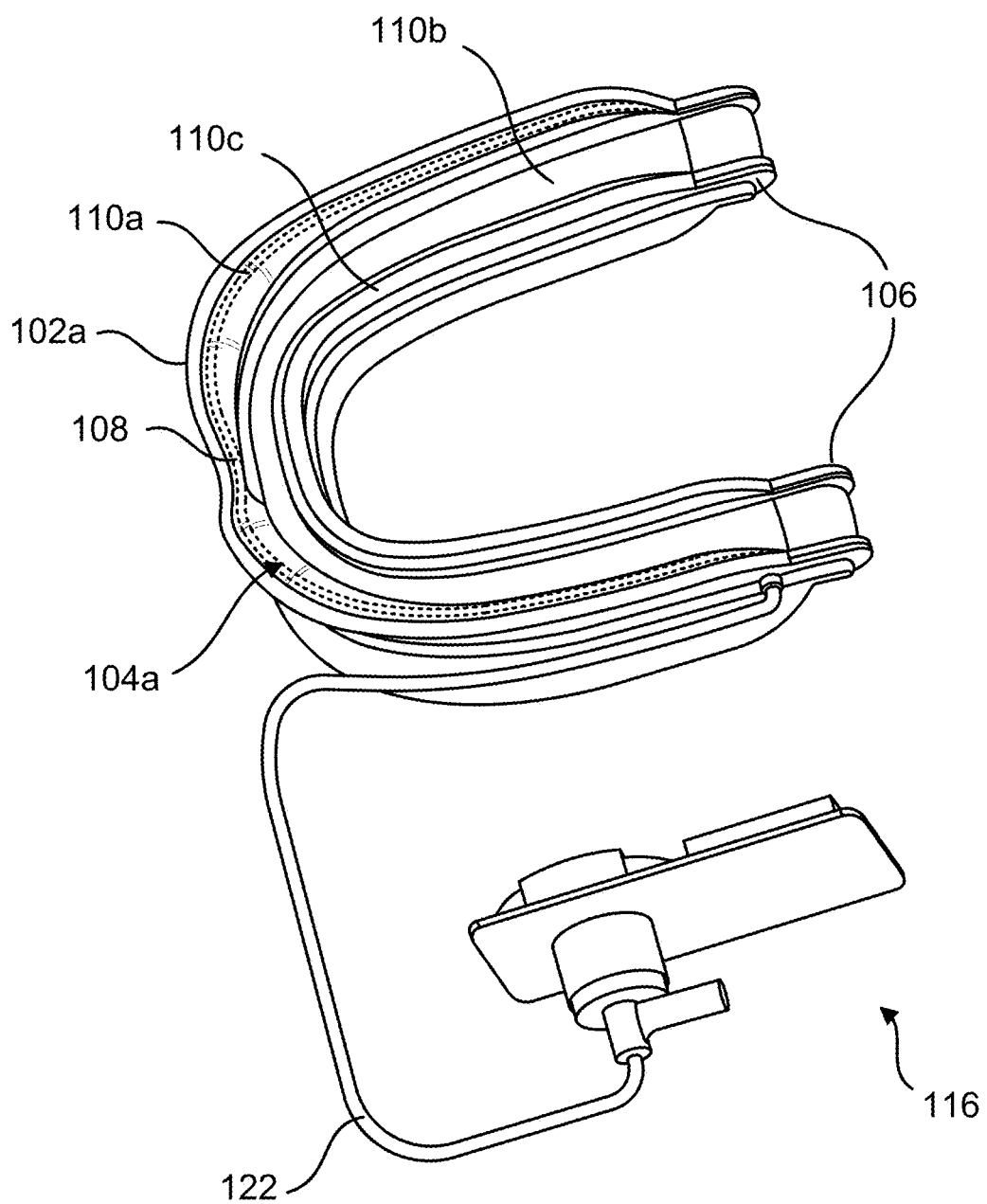
FIG. 4 depicts an angled top view of the device in accordance with embodiments of the invention.
Figure 5:
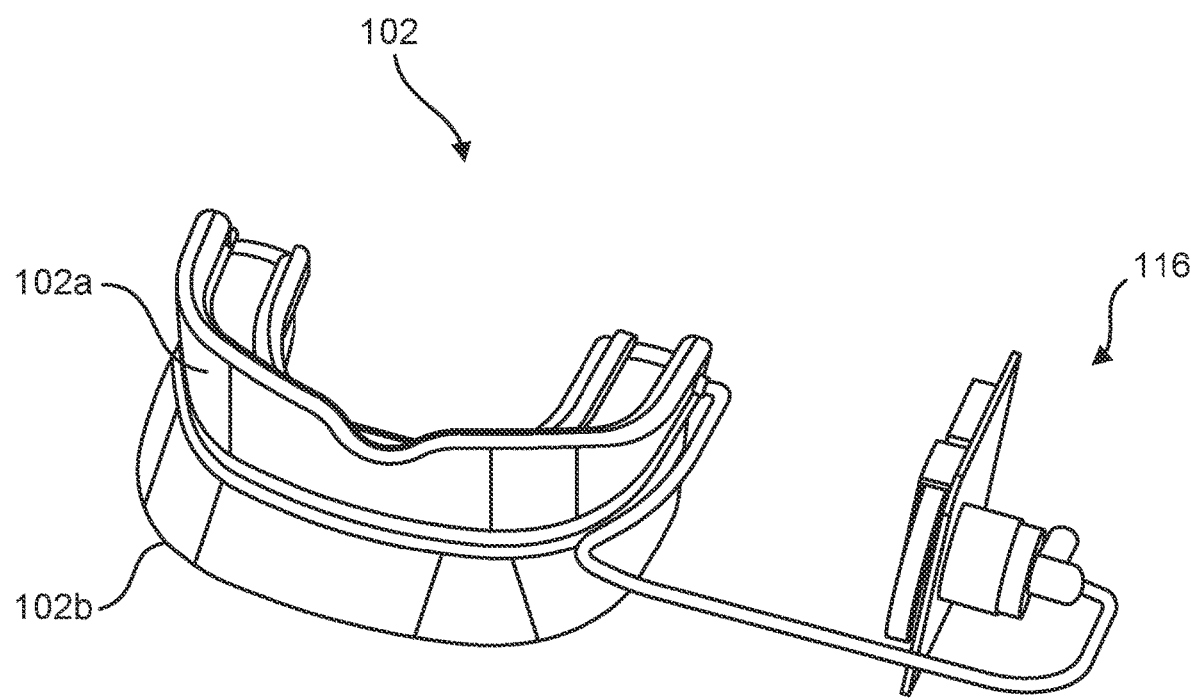
FIG. 5 depicts an angled front view of the device in accordance with embodiments of the invention.
Figure 6:
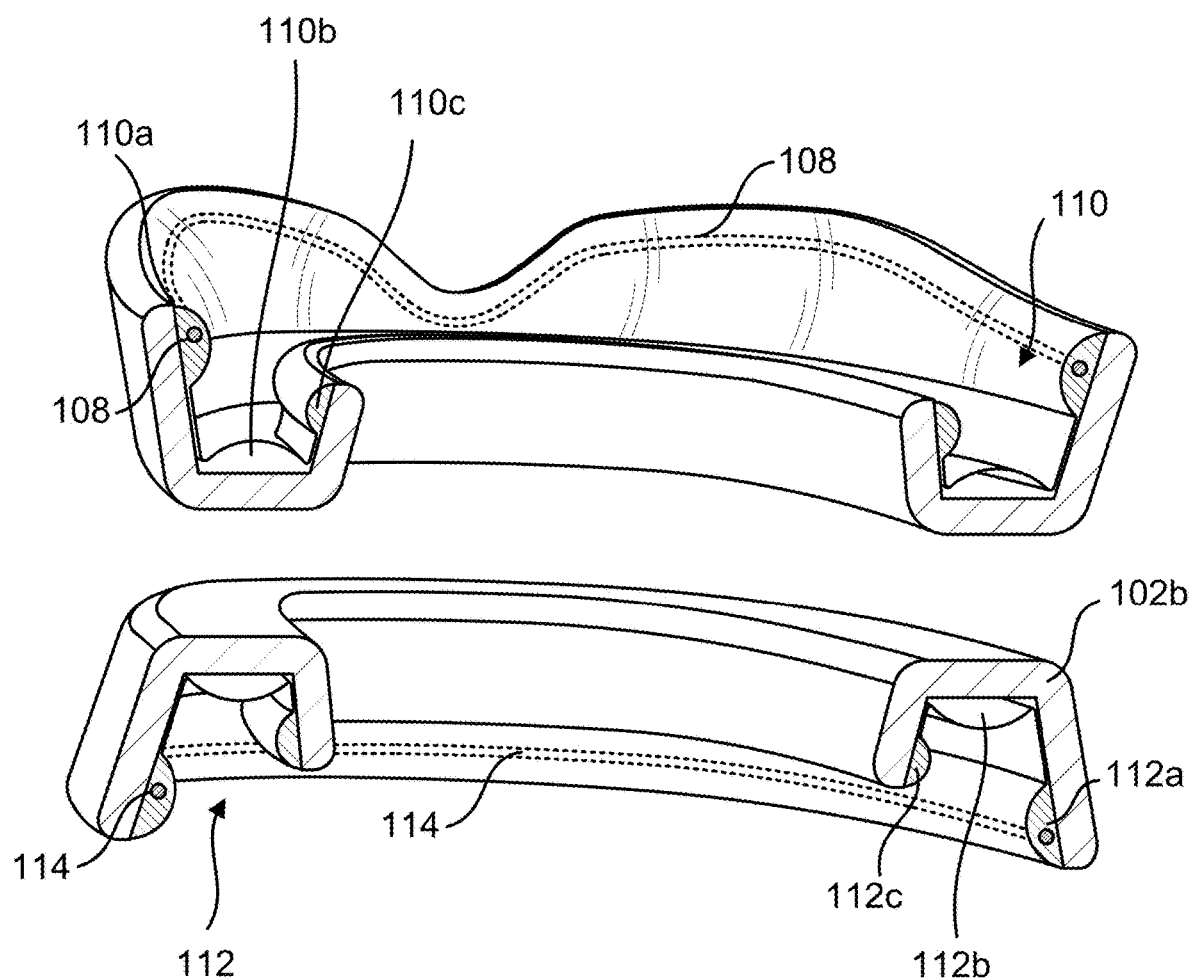
FIG. 6 depicts a cross section of the device in accordance with embodiments of the invention.

In the embodiment of the invention depicted in FIGS. 1-7, device 100 comprises a mouthpiece 102 with an upper component 102a and a lower component 102b. Upper component 102a and a lower component 102b may each have a U-shaped interior, 104a and 104b, that can accommodate the upper and lower rows of teeth, respectively. The upper component 102a and lower component 102b may be connected to one another by hinges 106 disposed at a molar end of the mouthpiece 102. The hinges may be spring like such that upper component 102a and lower component 102b are biased away from one another along the hinge path. This outward bias operates to hold upper component 102a against the upper row of teeth and the lower component 102b against the lower row of teeth, thereby preventing the mouthpiece from unintentionally falling out.

One advantage of the mouthpiece comprising a separate upper and lower component connected by hinges is a reduction in the impediment of a user's ability to breathe and speak that many mouthpieces have. The ability of the hinged connection to conform to the opening and closing of the mouth and the large space created between the upper and lower components of the mouthpiece provide these benefits. Further, the reduction in impediment to breathing and speaking not only makes the mouthpiece more comfortable for users but also decreases the chances that a player will remove the mouthpiece-either consciously or unconsciously. The removal of mouthpieces can lead to a player forgetting to replace their mouthpiece and may increase that player's chance of injury.

The upper component 102a comprises a first sensor 108 embedded in the upper component 102a. In some embodiments, a portion of first sensor 108 is exposed into the space defined by U-shaped interior 104a. In some embodiments, a portion of first sensor 108 is fully embedded in upper component 102a. The upper component 102a may comprise one or more inflatable upper balloons 110. The U-shape shaped interior 104a of upper component 102a may comprise an upper front balloon 110a, an upper tip balloon 110b, and upper back balloon 110c. The upper balloons 110 may be inflated with air, water, liquid or any other suitable medium via a valve, injection port or other suitable means. The upper balloons 110 are operable to be deflated via a valve, injection or other suitable means. Upper balloons 110 may be inflated after insertion of the mouthpiece in the mouth of a user to conform the interior of the upper component to the mouth, teeth and/or jaw to provide increased fixation. The inflation of upper balloons 110 further operates to press first sensor 108 against the maxilla of a user and hold first sensor 108 in a position. In some embodiments, first sensor 108 is located in a space of one of upper front balloon 110a, an upper tip balloon 110b, and upper back balloon 110c.

In some embodiments the upper component comprises between one and six inflatable balloons.

The lower component 102b may comprise a second sensor 114 embedded in the lower component 102b. In some embodiments, a portion of second sensor 114 is exposed into the space defined by U-shaped interior 104b. In some embodiments, a portion of first sensor 108 is fully embedded in lower component 102b. The lower component 102b may comprise one or more inflatable balloons 112. The U-shape shaped interior 104b of lower component 102b may comprise a lower front balloon 112a, a lower tip balloon 112b, and a lower back balloon 112c. The lower balloons 112 may be inflated with air, water, liquid or any other suitable medium via a valve, injection port or other suitable means. The lower balloons 112 are operable to be deflated via a valve, injection or other suitable means. Lower balloons 112 may be inflated after insertion of the mouthpiece in the mouth of a user to conform to the interior of the upper component to the mouth, teeth and/or jaw to provide increased fixation. The inflation balloons 112 further operate to press second sensor 114 against the mandible of a user and hold second sensor 114 in a position. Second sensor 114 may be in communication with first sensor 108. In some embodiments, second sensor 114 is located in a space of upper front balloon 110a, an upper tip balloon 110b, and upper back balloon 110c.

In some embodiments the lower component comprises between one and six inflatable balloons.

In some embodiments, the mouthpiece 102 may be customized to fit the mouth, teeth, jaws, mandible or maxilla of a user. The U-shaped interiors of the upper component may be customized, the U-shaped interiors of the lower component may be customized or both. The customization may be performed through molding, custom manufacture, inflatable portions or any suitable means known in the art. The customized fit of the mouthpiece may operate to provide better contact between a sensor and its intended point of measurement.

In some embodiments, the mouthpiece 102 comprises solely an upper component. In some embodiments, mouthpiece 102 comprises solely a lower component. In some embodiments, mouthpiece 102 may be a monolithic piece, without separate upper and lower components wherein the monolithic piece comprises upper and lower u-shaped cavities.

In some embodiments, only the upper component of the mouthpiece contains a sensor. In some embodiments, only the lower component of the mouthpiece contains a sensor. In some embodiments, both the upper component and the lower component of the mouthpiece contain a sensor.

The first sensor 108 may be connected with a computer module 116. Computer module 116 may comprise a microprocessor, a communication component, memory, power supply, transmitter, and other necessary computation components. In the embodiment depicted in FIGS. 1-7, Computer module 116 is located separately from mouthpiece 102. In some embodiments, computer module 116 is attached to the inside of a helmet. In some embodiments the microprocessor, power source, transmitter, memory and other computation components are located in the mouthpiece or are embedded in the mouthpiece. In the depicted embodiment, the communication component is a wireless transmitter and receiver, such as Bluetooth®. In some embodiments, the communication component is a module capable of connection with a network, internet, and or a mobile/computer application. The power supply may be a battery. The power supply may be a rechargeable battery.

The communication functionality of device 100 allows for real-time transmission of data between device 100 and a remote device for viewing the data. In some embodiments, the sensor inputs are processed into viewer-ready output data by the computer module of device 100 before being transmitted to one or more remote viewing devices. In some embodiments, device 100 operates to transmit sensor data directly to a remote viewing device for processing and then the remote viewing device outputs the data in view-ready format. The data transmission capabilities of the device, whether by wireless transmission, Bluetooth® or any other suitable means, allows for the real-time monitoring of users of device 100 by one or more viewing devices. In the context of the sports application, this functionality allows trainers, coaches and staff to actively monitor one or more players during a game and be made aware the instant a concussion event occurs.

The devices are capable of being tagged so that viewing devices can identify which devices are associated with a certain user, player, etc. The device may have certain measurement thresholds, such that when the sensors of device 100 detect that threshold signal, an alert is sent to a viewing device that the threshold event occurred.

The first sensor 108 and/or second sensor 114 may be in communication with computer module 116 via a removably attachable wire 120. The ends of removably attachable wire 120 may be magnetically connectable to a sensor, computer module or any associated port thereof.

In some embodiments, device 100 may comprise one or more external sensors. In the embodiment depicted in FIGS. 1-7, the device comprises a single external sensor 120 connected to the externally located computer module 116. External sensor 120 may be attached to the interior of a helmet and may be positioned to contact the cranium of a user when the helmet is worn. External sensor 120 may be in communication with one or more mouthpiece sensors. In the embodiment depicted in FIGS. 1-7, external sensor 120 is in communication with both first sensor 108 and second sensor 114.

The first sensor 108 and second sensor 114 may be in communication with external sensor 120 via a removably attachable wire 122. Removably attachable wire 122 may comprise magnetic ends for quick connection to the sensors, computer module or any other component of the system.

In some embodiments, device 100 may use other suitable spring mechanisms instead of hinges or in conjunction with hinges. Suitable spring mechanisms include springs, memory foam, springs, leaf springs, etc.

In some embodiments, the device may be operable to interact with a mobile device, computer, mobile application, web application or computer application. The devices measurements, reports and outputs are accessible in real time.

For the purposes of promoting an understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the system (and components of the individual operating components of the system) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A device for detecting and measuring concussions in a user comprising:
    a mouthpiece comprising an upper portion and a lower portion;
    said upper portion comprising an upper wall;
    said lower portion comprising a lower wall;
    a sensor;
    at least one upper balloon disposed along said upper wall;
    at least one lower balloon disposed along said lower wall; and
    wherein when said mouthpiece is worn by a user and when said at least one upper balloon and said at least one lower balloon are inflated, said sensor is in contact with a portion of a maxilla and a mandible of the user;
    wherein the sensor is operable to measure one or more of pressure, force, acceleration, momentum, translation, impulse or impact;
    wherein the device detects and measures concussions in the user using the measured one or more of pressure, force, acceleration, momentum, translation, impulse, or impact.

2. The device of claim 1, wherein the sensor is a U-shaped wire.

3. The device of claim 1, wherein the sensor is embedded in said upper wall and said lower wall of the mouthpiece.

4. The device of claim 1, wherein the sensor is operable to be in contact with an anterior portion of the maxilla.

5. The device of claim 1, wherein the sensor is an O-shaped ring.

6. The device of claim 1, wherein inflation of said at least one upper balloon presses said sensor against a portion of the maxilla of the user.

7. The device of claim 1, wherein said sensor is operable to be in contact with an anterior portion of a mandible of the user.

8. The device of claim 1, wherein the sensor is in communication with a microprocessor and a power source.

9. The device of claim 1, wherein the sensor is in communication with a communication device.

10. The device of claim 9, wherein the communication device is a short-range wireless transmitter and receiver.

11. The device of claim 9, further comprising a microprocessor and a power source, and wherein the communication device, power source and microprocessor are operable to be attached to an inside of a helmet.

12. The device of claim 1, wherein the mouthpiece comprises a spring like mechanism operable to force the upper component away from the lower component.

13. The device of claim 1, wherein the sensor is located inside the at least one upper balloon and the at least one lower balloon.

14. The device of claim 1, further comprising an external sensor, said external sensor in communication with said sensor, wherein said external sensor is separate from the mouthpiece.

15. The device of claim 1, wherein said sensor provides continuous contact with said maxilla and said mandible of said user.

16. A device for detecting and measuring concussions in a user comprising:
    a mouthpiece comprising an upper portion and a lower portion, said upper portion comprising at least one upper balloon, said lower portion comprising at least one lower balloon;
    a sensor; and
    wherein when said mouthpiece is worn by a user and when said at least one upper balloon and said at least one lower balloon are inflated, said sensor is in contact with a maxilla and a mandible of the user;
    wherein said sensor is operable to measure one or more of pressure, force, acceleration, momentum, translation, impulse or impact
    wherein the device detects and measures concussions in the user using the measured one or more of pressure, force, acceleration, momentum, translation, impulse, or impact.

17. The device of claim 16, wherein said sensor is an O-shaped ring.

18. The device of claim 16, wherein said sensor is embedded in a wall of said mouthpiece.

19. The device of claim 16, wherein the sensor is operable to be in contact with an anterior portion of the maxilla.

20. The device of claim 16, wherein said sensor is operable to be in contact with an anterior portion of a mandible of the user.

* * * * *